United States Patent [19]

Tollerud et al.

[11] Patent Number: 4,700,699
[45] Date of Patent: Oct. 20, 1987

[54] NURSING PAD

[76] Inventors: Bruce A. Tollerud; Carol R. Tollerud, both of 308 2nd St. SE. #203, Osseo, Minn. 55369

[21] Appl. No.: 849,818

[22] Filed: Apr. 9, 1986

[51] Int. Cl.⁴ .............................................. A61F 15/00
[52] U.S. Cl. ................................................... 128/156
[58] Field of Search ....................... 128/156, 461, 460; 132/88.5

[56] References Cited

U.S. PATENT DOCUMENTS

| | | | |
|---|---|---|---|
| 1,211,699 | 1/1917 | Guinzburg | 128/460 |
| 2,630,119 | 3/1953 | Aagesen | 128/461 |
| 2,748,771 | 6/1956 | Richards | 128/460 |
| 2,842,142 | 7/1958 | Peck | 132/88.5 |
| 2,891,544 | 6/1959 | London | 128/461 X |
| 4,047,534 | 9/1977 | Thomaschefsky | 128/461 |

Primary Examiner—Gregory E. McNeill
Attorney, Agent, or Firm—Merchant, Gould, Smith, Edell, Welter & Schmidt

[57] ABSTRACT

A nursing pad is disclosed having an absorbing pad of flexible absorbent material and configured to have a spaced apart first and second surface joined by a peripheral edge. The absorbing pad is sized to be placed over the front of a nursing woman's breast covering the nipple with side edges of the absorbing pad spaced apart for the side edges to remain on the front of the breast and with top and bottom edges of the pad placed against the upper and lower surface of the breast, respectively. A layer of moisture impervious material covers the second surface and extends around the side edges and bottom edge with the moisture impervious material having an opening exposing a portion of the first surface adjacent the nipple and with opposing surfaces of the material at the bottom edge of the pad defining a fluid reservoir.

14 Claims, 11 Drawing Figures

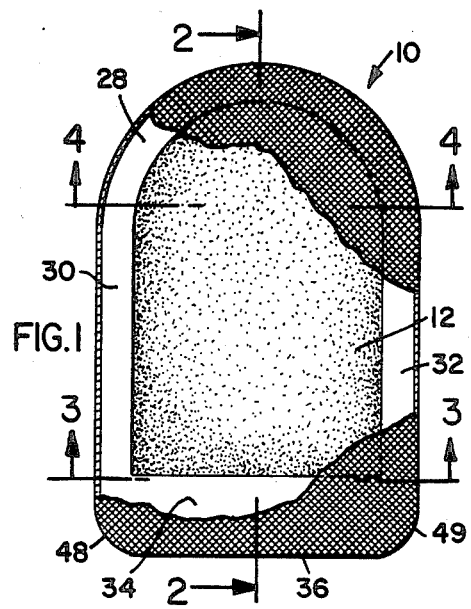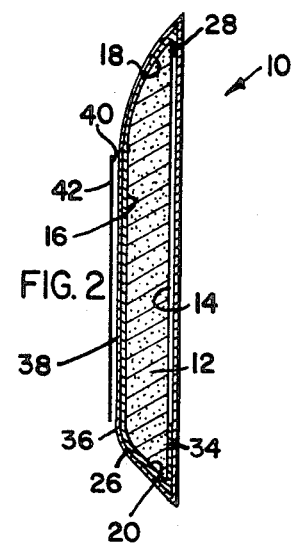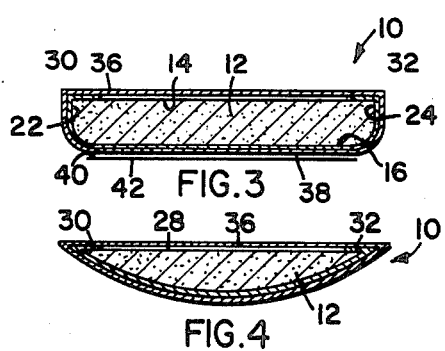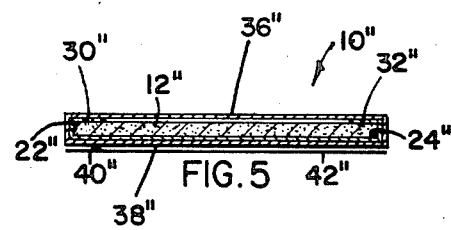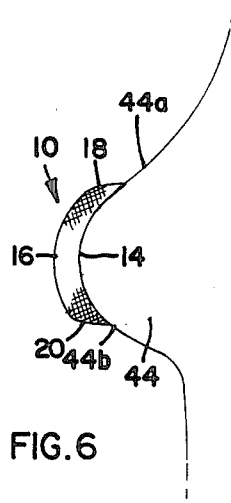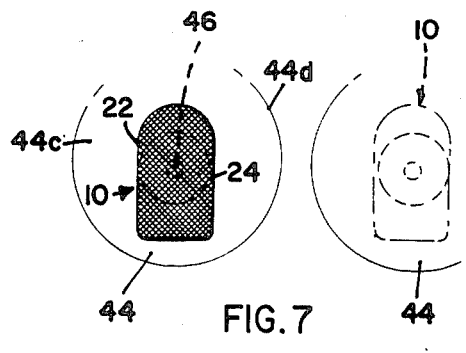

NURSING PAD

BACKGROUND OF THE INVENTION

I. Field of the Invention

This invention pertains to breast pads to be worn by nursing mothers. More particularly, this invention pertains to a nursing pad which is designed to minimize irritation and garment staining as well as being discreet during use.

II. Description of the Prior Art

During the latter stages of pregnancy and after child birth, it is very common for a mother to produce excess milk resulting in varying degrees of leaking which can cause discomfort and garment staining. For nursing mothers this problem is prolonged and lasts generally throughout the nursing period. The problem is most acute during the earlier stages of nursing. After nursing has progressed, the breasts commonly become regulated and leakage is reduced. However, the problem is not completely alleviated, and continued protection is necessary.

To improve the comfort and confidence of nursing mothers, nursing pads have become commercially available. The most common type of commercially available nursing pads are disk shaped pads of absorbent material. Such pads are frequently of multi-ply construction. An example of such a pad is shown in U.S. Pat. No. 4,047,534. Another such pad is shown in U.S. Pat. No. 4,074,721.

Nursing pads of the prior art share several disadvantages. One such disadvantage is that the shape of the pad does not readily conform with the shape of the breast. When placed within the bra during use, the disk is forced to conform to the cup shape of the bra. When so deformed, the disk shaped pad will bunch up at various locations around its peripheral edge. This bunching is readily noticeable through the mother's clothing. Accordingly, the pads can not be used discreetly and nursing mothers become self-conscious of their appearance. Another problem associated with prior art nursing pads is they do not provide adequate security from leakage. Absorbed milk will commonly migrate through the peripheral edge of the pad and stain the mother's clothing. As a result of these disadvantages, it is often impossible for a nursing mother to feel secure in public.

In addition to the unsightly bunching of the pad and their propensities to leak, prior art nursing pads are also uncomfortable. Many prior art nursing pads are damp against the mother's skin. Also, the prior art pads have generally rough and pronounced edges which chafe and further discomfort the mother.

OBJECTS AND SUMMARY OF THE INVENTION

It is an object of the present invention to provide a nursing pad which in use conforms to the shape of the mother's breast with reduced visibility through the mother's clothing.

A further object of the present invention is to provide a nursing pad with structure abating leakage of fluid from the pad.

A yet further object of the present invention is to provide a nursing pad which reduces chafing of the mother's skin.

According to a preferred embodiment of the present invention, a nursing pad is disclosed having an absorbing pad of flexible absorbent material. The absorbing pad is configured to have a first surface and spaced apart second surface which are joined by a peripheral edge. The absorbing pad is sized for the first surface to be placed over the front of a nursing mother's breast and covering the nipple with spacing between side edges of the pad constrained for the side edges to remain on the front of the breast. A layer of moisture impervious material covers the second surface and extends around a bottom edge and side edges of the pad with absorbent material contained within the volume defined by opposing surfaces of the moisture impervious material defining a fluid reservoir disposed on a lower surface of the breast.

BRIEF DESCRIPTION OF THE DRAWINGS

FIG. 1 is an elevation view of a nursing pad of the present invention shown in approximate actual size and showing a surface of the pad intended to be disposed against a nursing mother's breast and showing a covering material partly broken away;

FIG. 2 is a view of the nursing pad of FIG. 1 taken along line 2—2;

FIG. 3 is a sectional view of the nursing pad of FIG. 1 taken along line 3—3;

FIG. 4 is a sectional view of the nursing pad of FIG. 1 taken along line 4—4;

FIG. 5 is a sectional view of a nursing pad according to a first alternative embodiment of the present invention;

FIG. 6 is a side elevation view showing the nursing pad of FIG. 1 in use;

FIG. 7 is a frontal view taken in elevation showing a nursing pad of the present invention in use;

DESCRIPTION OF THE PREFERRED EMBODIMENT

Figure 8:
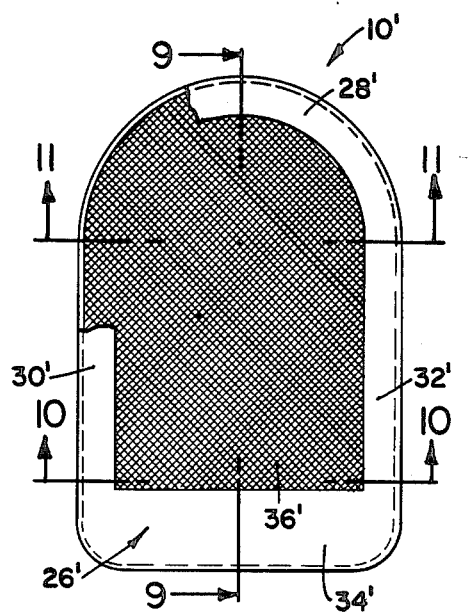
FIG. 8 is an elevational view of a second alternative embodiment of the present invention showing a surface of the pad intended for placement against a nursing mother's breast and showing a moisture impervious layer partly broken away.

With initial reference to FIGS. 1-4, a nursing pad according to the present invention is shown in a preferred embodiment. The nursing pad 10 includes an absorbing pad 12 of flexible absorbent material. An example of such a material would be absorbent cellulose fibers such as bleached wood pulp or fluff as are disclosed in U.S. Pat. No. 4,074,721. The absorbing pad is configured to have a first surface 14 and a spaced apart second surface 16. The first surface 14 and second surface 16 are joined by a peripheral edge which includes a top edge 18, a bottom edge 20 and two parallel spaced apart side edges 22 and 24 (all shown best in FIGS. 2 and 3). The top edge 18, bottom edge 20, side edges 22, 24, first surface 14 and second surface 16 cooperate to define a bounded volume of the absorbent material to absorb milk from a nursing mother.

The absorbing pad 12 is sized for the first surface 14 to be placed over the front of a nursing mother's breast and cover the nipple with the space between the side edges 22 and 24 constrained for the side edges to remain on the front of the breast. The top edge 18 and bottom edge 20 are spaced apart a distance sufficient for the top edge 18 to be disposed on the upper surface of the breast with the bottom edge 20 disposed on the lower surface of the breast. In order to retain the side edges 22 and 24 on the front of the breast, it is preferable that the width of the nursing pad 10 (i.e., the distance between side edges 22 and 24) be within a range of 2 to 2½ inches and preferably 2⅛ to 2⅜ inches. The length of the pad (i.e. the distance between edge 18 and edge 20) is preferably within the range of three to four inches.

As shown in FIG. 2, top edge 18 is a convex arc extending from the first surface 14 to the second surface 16. The bottom edge 20 extends upwardly at an angle from first surface 14 to second surface 16. Preferably an angle defined between bottom edge 20 and a line perpendicular to first surface 14 will be between 30 and 45 degrees. A preferred thickness of pad 12 (the maximum distance between surfaces 14 and 16) will be between three-eighths inch and one-half inch to maximize the volume for absorption while minimizing visibility of the pad through the mother's clothing.

As shown in FIG. 1, the top edge 18 is semicircular and convex extending from side edge 22 to side edge 24. Bottom edge 20 extends in a generally straight line between side edge 22 and side edge 24. As shown in FIGS. 3 and 4, the cross-section of the pad 10 above line 4—4 (i.e. above side edges 22,24) presents a convex second surface 16. The lower portion of the pad (e.g. at line 3—3) has a generally rectangular cross-section which gradually conforms to the cross-section of FIG. 4 as a cross-section is taken at any point between line 3—3 and line 4—4.

A layer of moisture impervious material 26 is provided covering the second surface 16 and extending around top edge 18, side edge 22, side edge 24 and bottom edge 20. Examples of such flexible moisture impervious materials are enumerated in U.S. Pat. No. 4,074,721. The material 26 does not cover first surface 14 but terminates to present a border of moisture impervious material on the first surface 14. The border includes a top border 28, a side border 30, a side border 32 and a bottom border 34 extending around top edge 18, side edge 24, side edge 22 and bottom edge 20, respectively. Opposing edges of the top border 28, side border 30, side border 32 and bottom border 34 define an opening exposing the first surface 14 of absorbing pad 12. The borders are dimensioned such that the opening they define is sufficiently large to permit easy placement of the pad. Additionally, the dimensioning of the bottom border 34 is also selected to provide a reservoir of adequate volume as will be described later. Preferably, borders 28, 30 and 32 will be between one-quarter inch and three-eighths inch wide. Bottom border 34 will have a width preferably between five-eighths inch and one inch.

As shown in the figures, the nursing pad 10 is provided with an outer layer 36 which is formed of moisture permeable non-absorbent material. Examples of such materials are described in U.S. Pat. No. 4,074,721 and a preferable material is described in U.S. Pat. No. 4,463,045. Outer layer 36 completely surrounds and encloses the moisture impervious material 26 and the absorbing pad 12. An outer surface 38 of material 36 which is adjacent surface 16 is provided with a layer of adhesive 40. A layer of paper or plastic backing 42 sized to cover adhesive layer 40 is removably placed over adhesive 40.

Use of the nursing pad will now be described with reference to FIGS. 1-4 and FIGS. 6 and 7. The nursing pad 10 is placed over the front of the mother's breast 44 with the nipple 46 disposed against outer layer 36 adjacent the exposed first surface 14. The backing 42 is removed to expose adhesive 40. With the pad 10 so disposed on breast 44 and with backing 42 removed, the mother's bra (not shown) will urge the pad 10 to conform to the shape of the breast 44 as shown in FIG. 6. Due to the curvature of top edge 18, top edge 18 causes a smooth unobtrusive transition from the upper surface 44a of the breast 44 to the outer surface 16 of the pad 10. Likewise, the angle at bottom edge 20 also provides smooth transition from the outer surface 16 of the pad 10 to the bottom surface 44b of the breast 44. The constrained distance between side edges 22 and 24 insures that no portion of the pad extends over the sides 44c, 44d of the breast as shown in FIG. 7. Accordingly, there is no bunching of the pad 10 which would be noticeable through the mother's clothing. Positioning of the nursing pad 10 on the front of the breast 44 is maintained by adhesive 40 which releasably sticks to the inner surface of the bra to retain the pad 10 in place.

As shown in FIG. 6, bottom edge 20 is disposed beneath the nipple 46. So disposed, opposing surfaces of the moisture impervious material 26 including bottom border 34 and side borders 30 and 32 at bottom edge 20 define a volume which opens away from bottom edge 20. The volume of absorbing pad 12 within this volume defines a fluid reservoir for receiving and retaining milk discharged by the mother. As the mother discharges milk, the outer layer 36 of moisture permeable non-absorbent material permits the milk to pass through the outer layer 36 where it is wicked into the material of absorbing pad 12. As the amount of fluid within the absorbing pad 12 increases, the fluid has a natural tendency to flow under gravity toward bottom edge 20. Flowing milk is contained within absorbing pad 12 by reason of the moisture impervious layer 26 which wraps around side edges 22, 24 and bottom edge 20. At bottom edge 20, the moisture impervious material 26 with enlarged bottom border 34 defines an enlarged volume reservoir to retain collected fluid. As a result of the wrap around material 26, and the reservoir, fluid is contained within the absorbent pad 12 such that is may not stain the mother's clothing. As the absorbing pad becomes saturated with fluid, the fluid will seep through the outer layer 36 at the upper edge of bottom border 34. The mother will sense this liquid against her skin and may replace the nursing pad 10 before the fluid seepage has an opportunity to stain her clothing.

As shown in FIGS. 3 and 4, the cross-section of the pad 12 varies from a rectangular cross-section at the bottom edge 20 to a generally convex section at the top edge 18. The convex shape at top edge 18 provides smooth curvature of the pad 12 to reduce its visibility in use. A pad could be formed such that this convex cross-section would extend to the bottom edge 20. However, this configuration reduces the volume of the pad 12 at the bottom edge 20 thereby reducing the fluid containing capacity of the reservoir defined between opposing surfaces of the impervious material 26. Also, the relatively flat surface of surface 16 in the region between side edges 22 and 24 provides a good surface for adhesive 40 and backing 42.

As shown in FIGS. 1 and 3, the pad is provided with rounded edges 48 and 49 at the point of juncture between bottom edge 20 and side edges 24 and 22, respectively. These rounded edges provide smooth contoured surfaces adjacent the mother's skin to prevent chaffing and irritation.

The nursing pad of FIGS. 1–4 provides for a thick layer of absorbing material 12 with contoured peripheral edges selected to insure continuous unobtrusive conformity between the pad and the mother's breast. As a result, the volume of absorbing material 12 is maximized without sacrificing the desire to have a pad which minimizes its appearance through the mother's clothing.

After the mother has been nursing for a period of time, the breasts typically become self-regulating such that the amount of discharge is reduced. When this occurs, a thinner pad of absorbing material can be employed which further enhances the visual obscurity of the pad during use. In such a case, an absorbing pad 12" having a thickness between one-eighth inch and one-quarter inch may be used in the form of a rectangle having its side edges 22", 24" spaced apart a distance similar to that of side edges 22 and 24 to insure that the pad 10" remains on the front of the breast without being forced to contour over onto the sides of the breast. Such a pad is shown in FIG. 5 with like elements being assigned like numerals with the addition of double apostrophes.

Figure 9:
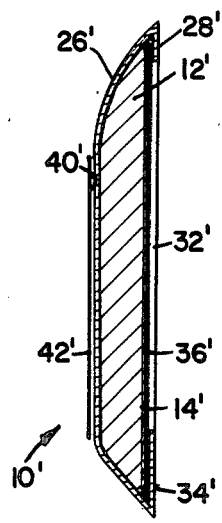
FIG. 9 is a view of the nursing pad of FIG. 8 taken along line 9—9.
Figure 10:
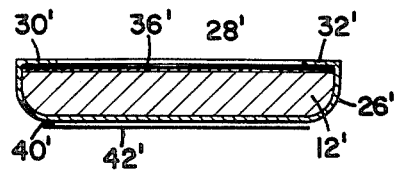
FIG. 10 is a view of the nursing pad of FIG. 8 taken along line 10—10.
Figure 11:
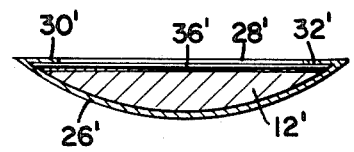
FIG. 11 is a view of the nursing pad of FIG. 8 taken along line 11—11.

FIGS. 8–10 show a second alternative embodiment similar to the embodiment shown in FIGS. 1–4 with similar elements being assigned similar identifying numerals with the addition of single apostrophes. The embodiment of FIGS. 8-11 differ from that of FIGS. 1–4 in that the layer of moisture permeable non-absorbent material does not surround the pad 12'. Instead, a layer of moisture permeable non-absorbent material 36' is disposed on the first surface 14' of pad 12'. The borders 30', 32', 28' and 34' capture the layer 36' on surface 14' with opposing edges of the borders defining an area of material 36' covering surface 14' and sized to be placed on a mother's breast covering the nipple. Adhesive 40' is applied to the moisture impervious material 26' on a side thereof adjacent second surface 16'. By placing layer 36' between the impervious layer 26' and surface 14', liquid will flow between layer 36' and bottom border 34' thereby keeping the mother's skin dry.

From the foregoing detailed description of the present invention, it has been shown how the objects of the invention have been obtained in a preferred manner. For example, it has been shown how the structure and size constraints of the nursing pad 10 provide for a nursing pad which does not bunch up when forced to conform with the mother's breast such that it does not show through the mother's clothing. Additionally, the wrap around moisture barrier 26 prevents seepage of fluid through the peripheral edges of the pad to further enhance the security and confidence of the mother. Finally, the moisture permeable non-absorbent layer 36 and contouring of the pad also provide enhanced comfort for the mother during use.

While the foregoing is a detailed description of the preferred embodiment, modifications and equivalents of the disclosed concepts such as readily occur to those skilled in the art are intended to be included in the scope of this invention. Thus, the scope of this invention is intended to be limited only by the scope of the claims as are or may hereafter be appended hereto.

What is claimed is:

1. A nursing pad for nursing women comprising:
an absorbing pad of flexible absorbent material; said absorbing pad configured to a first surface and a spaced apart second surface and a peripheral edge joining said first and second surfaces; said peripheral edge and surfaces defining a bounded volume of said absorbent material and said peripheral edge including a top edge portion, a bottom edge portion, a first side edge portion and a second side edge portion;
said absorbing pad sized for said first surface to be placed over the front of a nursing woman's breast and covering the nipple with spacing between said side edge portions sized for said side edge portions to remain on the front of said breast; said top and bottom edge portions spaced apart for said top edge portion to rest upon an upper surface of said breast and said bottom edge portion disposed against a lower surface of said breast; a layer of moisture impervious material covering said second surface and extending around said bottom edge portion, said moisture impervious material sized to extend around said bottom edge portion and extend opposing said second surface and said side edge portions; opposing surfaces of said moisture impervious material defining a fluid containing volume at said bottom edge portion with absorbent material disposed within said volume providing a fluid reservoir; said volume having a reservoir opening facing in a direction opposing said top edge; said pad having an intended nipple opposing area for placement against said nipple when said pad is disposed upon said breast in a predetermined desired position; said moisture impervious material first terminating at a location on said surface between said bottom edge and said nipple opposing area.

2. A nursing pad according to claim 1 wherein said top edge portion is convex extending from said first surface to said second surface.

3. A nursing pad according to claim 2 wherein said top edge portion is an arc of a circle extending between said side edge portions.

4. A nursing pad according to claim 1 wherein said nursing pad includes a layer of non-absorbent fluid permeable material disposed on sid first surface.

5. A nursing pad according to claim 1 wherein said nursing pad is provided with a layer of adhesive on an exposed surface facing in a direction away from said breast when said pad is disposed in said predetermined desired position.

6. A nursing pad according to claim 4 wherein said layer of non-absorbent fluid permeable material is disposed on said first surface and extending between said first surface and in opposing surface of said layer of moisture impervious material.

7. A nursing pad according to claim 1 wherein said layer of moisture impervious material extends around said side edges.

8. A nursing pad according to claim 1 wherein said layer of moisture impervious material extends around said top edge.

9. A nursing pad comprising:
an absorbing pad of flexible absorbent material; said absorbing pad configured to a first surface and spaced apart second surface with a peripheral edge joining said first and second edges; said peripheral edge including a pair of generally parallel spaced apart side edges with one end of said side edges joined by a top edge and an opposite end of said side edges joined by a bottom edge;

said absorbing pad sized for said first surface to be placed against the front of a woman's breast covering the nipple with the distance between said side edges selected for said side edges to be disposed on the front of the breast and with the distance between said top and bottom edges selected for said top edge to be placed against the breast above the nipple and the bottom edge placed against the breast below the nipple; a layer of moisture impervious material covering said second surface and extending around said side edges and said bottom edge, said pad having an intended nipple opposing area for placement against said nipple when said pad is disposed upon said breast in a predetermined desired position, said moisture impervious material terminating at a location on said first surface between said bottom edge and said nipple opposing area, opposing surfaces of said moisture impervious material defining a reservoir of absorbent material beneath the breast and separated from the breast by said material with said reservoir having an opening disposed to receive fluid from said nipple opposing area and retains said fluid within said reservoir.

10. A nursing pad according to claim 9 wherein said top edge is an arc of a circle extending between said side edges.

11. A nursing pad according to claim 9 wherein said top edge is convex extending from said first edge to said second surface in a direction toward said bottom edge.

12. A nursing pad according to claim 9 wherein said nursing pad includes a layer of non-absorbent fluid permeable material disposed on said first surface.

13. A nursing pad according to claim 9 wherein said nursing pad is provided with a layer of adhesive on an exposed surface facing in a direction away from said breast when said pad is disposed in said predetermined desired position.

14. A nursing pad according to claim 12 wherein said layer of non-absorbent fluid permeable material is disposed on said first surface and extending between said first surface and an opposing surface of said layer of moisture impervious material.

* * * * *